United States Patent [19]
Kahn

[11] 4,044,468
[45] Aug. 30, 1977

[54] HANDLE FOR CUTTING AND ABRADING INSTRUMENTS USEFUL IN THE PRACTICE OF ENDODONTIA

[76] Inventor: Henry Kahn, 366 Dell, Highland Park, Ill. 60035

[21] Appl. No.: 682,361

[22] Filed: May 3, 1976

[51] Int. Cl.² .............................................. A61C 5/02
[52] U.S. Cl. ........................................................ 32/57
[58] Field of Search ............................ 32/57, 58, 40 R

[56] References Cited
U.S. PATENT DOCUMENTS

| 3,247,594 | 4/1966 | Nosonowitz | 32/57 |
| 3,562,913 | 2/1971 | Saffro | 32/57 |

*Primary Examiner*—Robert Peshock

[57] ABSTRACT

Improved handle means for files and reamers employed in the practice of endodontics to enable more dependable grip by the operator and to signal the operator that a desired position of the cutting surfaces is being maintained.

2 Claims, 12 Drawing Figures

U.S. Patent  Aug. 30, 1977  4,044,468
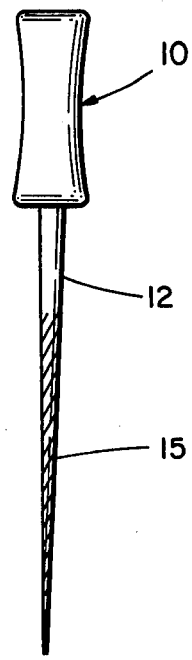
FIG.1
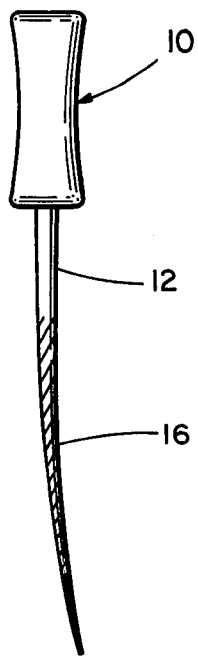
FIG.2
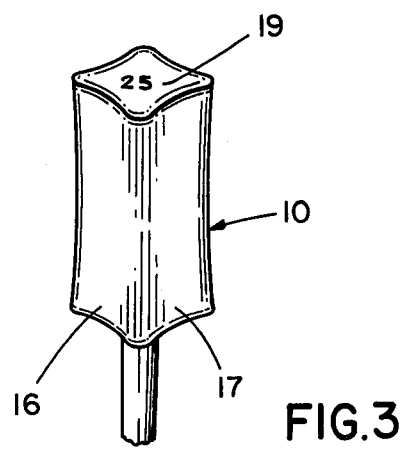
FIG.3
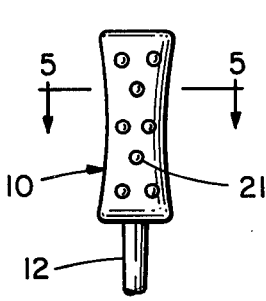
FIG.4
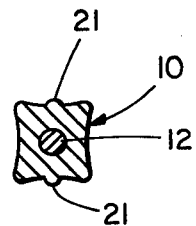
FIG.5
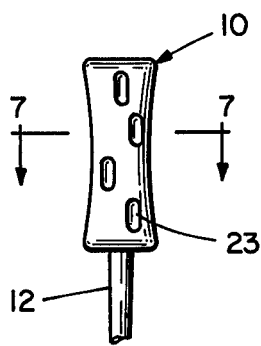
FIG.6
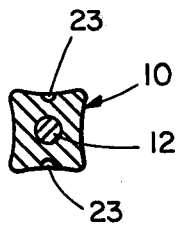
FIG.7
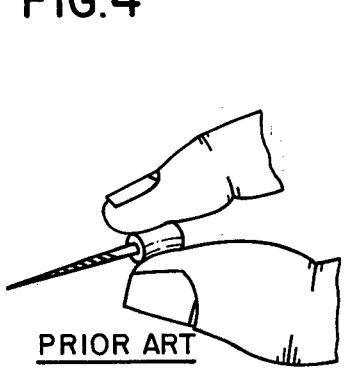
FIG.9
PRIOR ART
FIG.8
PRIOR ART
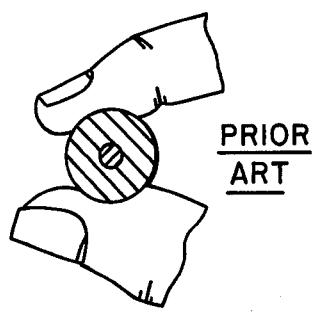
FIG.10
PRIOR ART
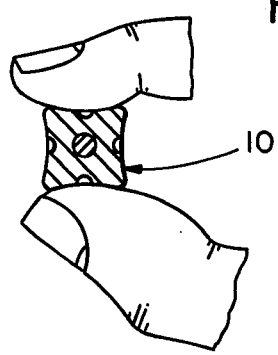
FIG.11
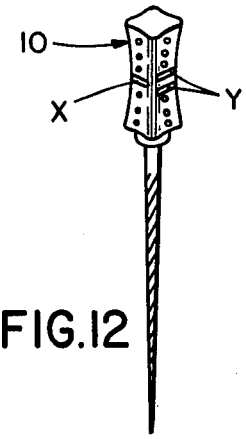
FIG.12

HANDLE FOR CUTTING AND ABRADING INSTRUMENTS USEFUL IN THE PRACTICE OF ENDODONTIA

BACKGROUND OF THE INVENTION

In the practice of root canal therapy, sometimes referred to as endodontia, it becomes necessary to scrape or abrade the wall of the canal prior to filling the same. Such removal is accomplished by using what are termed "files" or "reamers" which are reciprocated manually within the canal to prepare the same for the filling step by cleaning and shaping. Since the implements employed, whether files or reamers, function in essentially the same way, it will be convenient, for conciseness in the instant disclosure, to refer to the same broadly as "files". The implement is provided with a handle to improve the grip. Although, a mechanical apparatus to perform this digital function is known, it has not met with acceptance, no doubt for the reason that optimum control of the tool is a matter of feel through the fingertips. The importance of reliable grip and feel becomes even more evident when it is remembered that a typical file is approximately 25 mm. in length measured outwardly from the handle and that a typical handle is about 3 to 4 mm. in diameter and 8 to 9 mm. in length. Although operators use a rubber dam to preclude swallowing by the patient of a dropped file, there is nevertheless an everpresent hazard which it is necessary to anticipate and avoid by assuring a firm but sensitive grip.

Present forms of handle are cylindrical and, therefore, are not conducive to reliable gripping.

SUMMARY OF THE INVENTION

The present invention, in one aspect, provides a handle for an implement as aforesaid in which gripping thereof between the index finger and thumb is greatly facilitated by providing concavities on four sides, the concavities having a curvature not only to enable comfortable seating of the tip of the finger and thumb but to defeat any tendency of the implement to shift axially. As a further measure, the invention, in another aspect, provides for distinguishing between the two pairs of opposite faces by depressions in the surface. Thus, two opposite faces of a handle, which has a substantially square cross section, may be provided with physical indicia such as recesses which signal to the operator that the file is located in a particular angular orientation about its principal axis. In this way, the operator is enabled to maintain that desired angular position of the file, i.e. in the case of a file which is arcuate along its length, the proper relationship of the file with respect to the root canal may be maintained notwithstanding the operator may be interrupted during the procedure. This result is readily achieved by tactile sensation, while using the implement.

Another object of the invention is to identify the four faces of the handle by means which will signal the operator that a known area of the teeth of the file is in use at a particular time. This result is preferably achieved by engraved or embossed indicia which are differentiated in a suitable manner.

BRIEF DESCRIPTION OF THE DRAWING

FIG. 1 shows a side elevation, somewhat enlarged, of a straight design of file incorporating my improved handle;

FIG. 2 shows a side elevation, similar to FIG. 1 but including a curved design of file;

FIG. 3 is a perspective view of an upper portion of FIGS. 1 or 2 to show my improved handle;

FIG. 4 is a modification of the handle of FIG. 3;

FIG. 5 is a cross section taken on the line 5—5 of FIG. 4;

FIG. 6 shows another modification of the handle of FIG. 3;

FIG. 7 is a cross section on the line 7—7 of FIG. 6;

FIG. 8 shows a file in accordance with the prior art;

FIG. 9 shows the same in use;

FIG. 10 illustrates a known form of handle of circular cross section;

FIG. 11 is a view similar to FIG. 10 but showing a handle embodying the principles of the invention; and FIG. 12 is a perspective view to illustrate one tactile mode of differentiating between the four faces of a handle in accordance with the invention.

BRIEF DESCRIPTION OF THE PREFERRED EMBODIMENTS

Adverting to FIGS. 1 to 3 the greatly enlarged file there shown comprises a handle 10, desirably of plastics composition, in which the shank 12 is embedded at the time of molding. The working portion of the file is indicated schematically at 15 and 16 respectively.

The invention handle, best seen in FIG. 3, includes two opposed pairs of gripping faces 16 and 17, all identical, each of the faces being concave in both senses, i.e. with respect to a vertical plane and with respect to a horizontal plane. Stated otherwise, a typical transverse, cross section normal to the longitudinal axis is a cushion shaped outline (See FIG. 5) and a typical longitudinal cross section is also cushion shaped. The doubly concave surfaces indicated by the numerals 16 and 17 present saucer-shaped pads to receive the doubly-convex configuration of the tip of the human thumb and index finger. The top and bottom faces of the handle may be of any desired configuration except that it may be desirable to have the top face flat to receive numerals, letters or symbols 19 identifying the file as to size and other characteristics.

From the foregoing it will have been comprehended that the instrument is precluded from slipping during use since the handle is adapted to fit naturally in the position where digital engagement is principally in the region of minimum cross section (FIG. 9).

As pointed out above it is desirable to provide means maintaining the implement in a predetermined angular sense, referred to the longitudinal axis. For example, when using a curved file (FIG. 2) it is advantageous, if not essential, to hold the file in a position whereat the file will cut on a convexity or concavity in the root canal. This object is attained with the present invention by providing protuberances 21—21 on two opposite faces of the handle 10 (FIGS. 4 and 5). These thus-identified faces are readily distinguishable by the tactile sense of the operator and the angular orientation of the file thus established and maintained.

FIGS. 6 and 7 illustrate an alternative form in which the protuberances 21 are replaced by recesses 23. Otherwise the function is the same as in FIGS. 4 and 5.

FIG. 8 has been included to indicate in essentially full size the magnitude of a typical commercial file; of a type in common use.

FIG. 10 is a view similar to FIG. 9 but with a handle of circular outline as known in the prior art, whereas FIG. 11 shows the invention handle. In particular, it will be observed that the doublyconcave faces of the handle enable natural nesting of the fingertips in the respective concavities. The operator's fingers are subjected to less tension with consequent decreased fatigue.

It will be understood that, as the file becomes dull, it is desirable to distribute the wear by presenting unworn or relatively unworn teeth to the work. The operator is aided in so doing by relating the toothed end of the file to a definite angular position. Thus, the useful life of the file is lengthened and costs reduced.

From the foregoing description it will have become apparent that the invention implement has a two-fold advantage, namely, the implement is reliably retained in a longitudinal direction to preclude slippage relative to the fingers and the implement is easily oriented angularly about its longitudinal axis.

The square shape of the handle is also of advantage in preventing rolling of the implement on the bracket tray.

In order to relate the angular orientation of the implement to the operator's fingers, I provide coding as illustrated in FIG. 12. Each face of the handle is coded by means of embossed or engraved transverse lines indicated at X and Y. The letter X is a single line and Y is a double line. The other two faces have triple and quadruple lines respectively (not shown). By palpating these lines, the operator can readily discriminate between them and orient the file accordingly. Not only is this feature important in relating longitudinal curvature of a file to a longitudinally curved root canal but, in the case of a straight canal, enables uniform wear of the file by rotating the same from one position to another. This, in turn, leads to maximum use of the file teeth and consequent economy.

I claim:

1. A file useful in root canal therapy comprising a toothed working end and a shank end, said shank end having a hangle attached thereto to be held between the thumb and index finger, said handle having two pairs of opposite faces, each of said faces being doubly concave inwardly and said faces being further characterized by different surface discontinuities for tactile differentiation therebetween.

2. A file useful in root canal thereapy comprising a toothed working end and a shank end, said shank end having a handle attached thereto to be held between the thumb and index finger, said handle having two pairs of opposite faces, each of said faces being doubly concave inwardly and said faces being further characterized by surface indicia individual to each face which may be felt by the fingertips to signal the operator the thenorientation of the file about its longitudinal axis.

* * * * *